United States Patent [19]

Kato

[11] Patent Number: 5,010,875

[45] Date of Patent: * Apr. 30, 1991

[54] INTRAVASCULAR ENDOSCOPE APPARATUS

[75] Inventor: Shinichi Kato, Oome, Japan

[73] Assignee: Olympus Optical Co., Ltd., Tokyo, Japan

[*] Notice: The portion of the term of this patent subsequent to Jun. 19, 2007 has been disclaimed.

[21] Appl. No.: 526,841

[22] Filed: May 22, 1990

Related U.S. Application Data

[63] Continuation of Ser. No. 356,996, May 25, 1989, Pat. No. 4,934,339.

[30] Foreign Application Priority Data

Oct. 7, 1988 [JP] Japan .................. 63-252958

[51] Int. Cl.$^5$ .............................. A61B 1/04
[52] U.S. Cl. ............................ 128/6; 358/98
[58] Field of Search .................. 128/4, 6; 358/98

[56] References Cited

U.S. PATENT DOCUMENTS

| 4,569,335 | 2/1986 | Tsuno | 128/6 |
| 4,651,202 | 3/1987 | Arakawa | 128/6 X |
| 4,934,339 | 6/1990 | Kato | 128/6 |

FOREIGN PATENT DOCUMENTS 61-259635 11/1986 Japan .

Primary Examiner—William H. Grieb
Attorney, Agent, or Firm—Frishauf, Holtz, Goodman & Woodward

[57] ABSTRACT

When an insert portion of an endoscope main body is inserted into a blood vessel of a patient and an observed image in the blood vessel is recorded by an image recording unit such as a TV camera and a video tape recorder, the image observed by the endoscope main body is detected by a red-only detector. When it is confirmed that a field of view in the blood vessel can be assured in accordance with a detection result of the red-only detector, the image recording unit is turned on. When the field of view cannot be assured, the image recording unit is turned off.

13 Claims, 4 Drawing Sheets

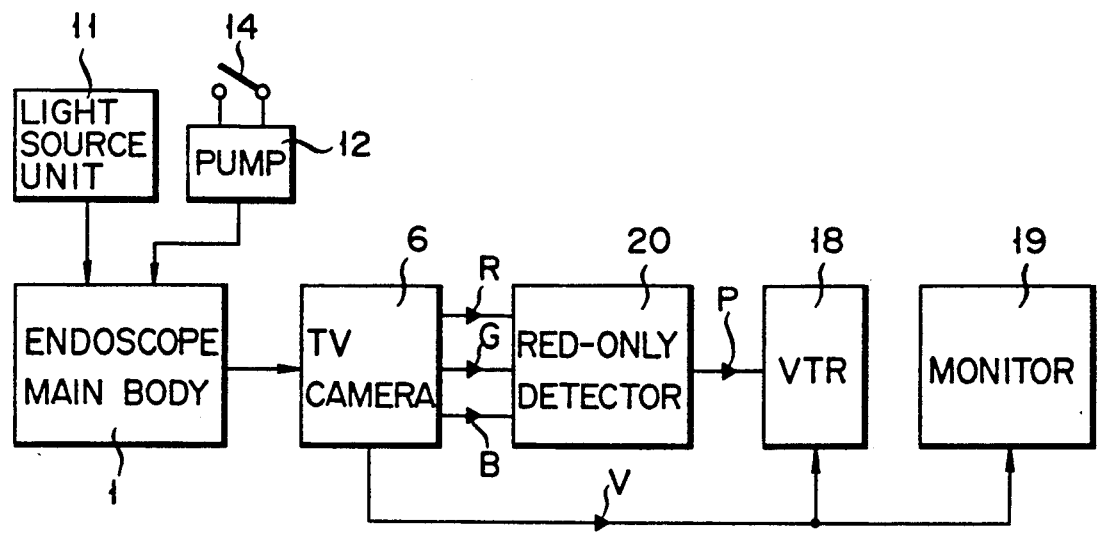
F I G. 2
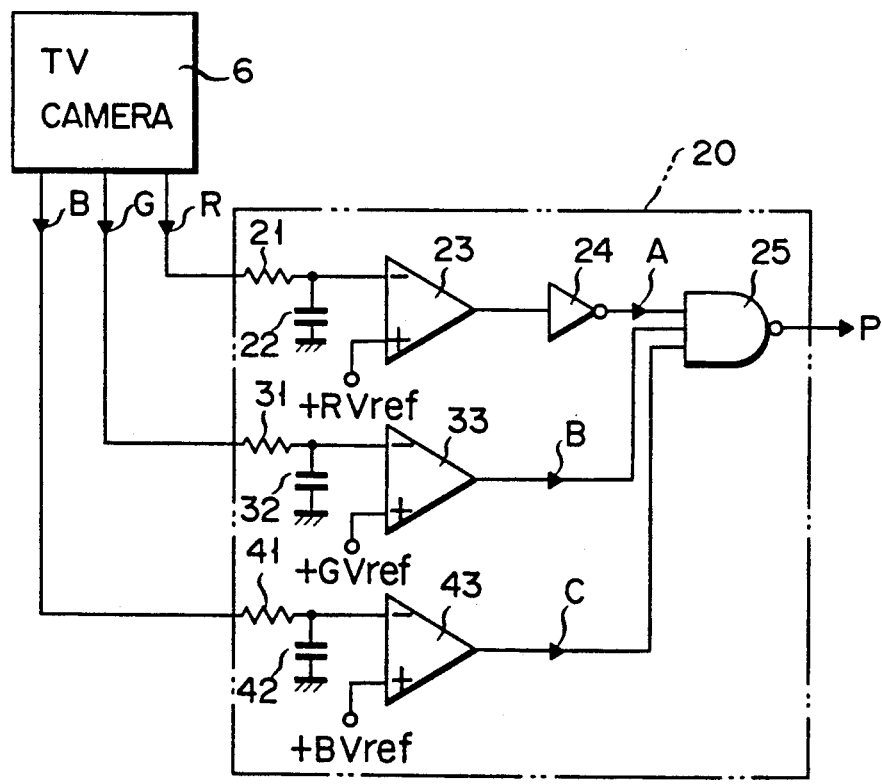
F I G. 3

INTRAVASCULAR ENDOSCOPE APPARATUS

This is a continuation of application Ser. No. 07/356,996 filed May 25, 1989 now U.S. Pat. No. 4,934,339, issued June 19, 1990.

BACKGROUND OF THE INVENTION

1. Field of the Invention

The present invention relates to an intravascular endoscope apparatus for observing the interior of a blood vessel of a patient.

2. Description of the Related Art

A method using an intravascular endoscope is known as a means for observing the interior of a blood vessel of a patient. In this method, a blood vessel of a patient is partially incised, and an insert portion of the intravascular endoscope is inserted into the blood vessel through the incised portion to observe the interior of the blood vessel. In this case, the blood in the blood vessel interferes with a field of view. Therefore, a physiological saline solution is sprayed into the blood vessel from a distal end portion of the insert portion of the intravascular endoscope, and the blood in the field of view is temporarily scattered. While the field of view is assured in this state, observation is performed.

An image observed by the intravascular endoscope can be recorded on a photograph or a video tape. However, as described above, a recording operation need be performed within a moment when the physiological saline solution is sprayed into the blood vessel to scatter the blood, and the field of view is assured.

As described above, however, an operation for spraying the physiological saline solution from the intravascular endoscope and an operation for recording the observed image are performed by manual operations of an operator. For this reason, it is difficult to perform an accurate and stable recording operation.

In order to solve the above problem, as disclosed in Japanese Patent Disclosure (Kokai) No. 61-259635, a spray operation of a physiological saline solution and a recording operation of an image are automatically performed at predetermined timings based on an operation by an operator.

A time lag is present until the field of view in the blood vessel is assured after the spray operation of the physiological saline solution is started. In addition, this time lag varies depending on the length of a tube for the physiological saline solution, the pressure of a pump, and an influence of a blood pressure of a patient.

In the above-described conventional endoscope, therefore, since a recording operation is undesirably started before the field of view is assured even if the spraying operation of the physiological saline solution and the recording operation of the image are performed at proper timings, a film or a video tape serving as a recording medium is wasted.

In the above-described conventional endoscope, the spray operation of the physiological saline solution and the recording operation of the image are synchronously stopped. However, even if the spray operation of the physiological saline solution is stopped, the field of view is not abruptly lost. As a result, an effective image is undesirably missed.

More specifically, although it is preferable that the spraying operation of the physiological saline solution and the recording operation of the image are completed within a short period of time, the recording operation must be repeated in a state wherein the effective image is missed as described above, thus prolonging the recording time.

SUMMARY OF THE INVENTION

It is an object of the present invention to provide an intravascular endoscope apparatus for causing a color tone detector to detect whether a field of view is assured during observation of an image in a blood vessel, recording an observed image when the field of view is assured, stopping a recording operation when the field of view is not assured or when an unnecessary image is observed so that waste of a recording medium can be prevented, and for recording a necessary and effective image without failure, thus decreasing a recording time.

According to the present invention, there is provided an intravascular endoscope apparatus comprising an endoscope main body, including an insert portion to be inserted in a blood vessel, for observing the interior of the blood vessel, a fluid supply unit, connected to the endoscope main body, for spraying a fluid from the insert portion, and an image recording unit for recording an image observed by the endoscope main body, wherein the interior of the blood vessel is observed by the endoscope main body while a field of view is assured by scattering blood in the blood vessel by the fluid sprayed from the insert portion.

According to the present invention, the endoscope main body causes a color tone detector to detect whether the field of view is assured during observation of the interior of the blood vessel. When the field of view is assured, the image recording unit is turned on and the observed image is recorded. When the field of view is not assured, the image recording unit is turned off and the observed image is not recorded.

The image recording unit includes a TV camera and a video tape recorder. Only when the image recording unit is turned on in response to a signal from the color tone detector, a video signal is recorded on a video tape.

The color tone detector comprises a red-only detector, and the red-only detector receives red, green, and blue video signals from the TV camera. This red-only detector detects only a red image serving as a specific image, and the video tape recorder is turned off.

In the image recording unit, a still camera may be employed in place of the video tape recorder. Only when the image recording unit is turned on in response to a signal from the color tone detector, the observed image is recorded on a film.

BRIEF DESCRIPTION OF THE DRAWINGS

FIG. 2 is a block diagram of the first embodiment;

FIG. 3 is a circuit diagram of a red-only detector in the first embodiment;

DETAILED DESCRIPTION OF THE PREFERRED EMBODIMENTS

A first embodiment of the present invention will be described hereinafter with reference to FIGS. 1 to 4.

Figure 1:
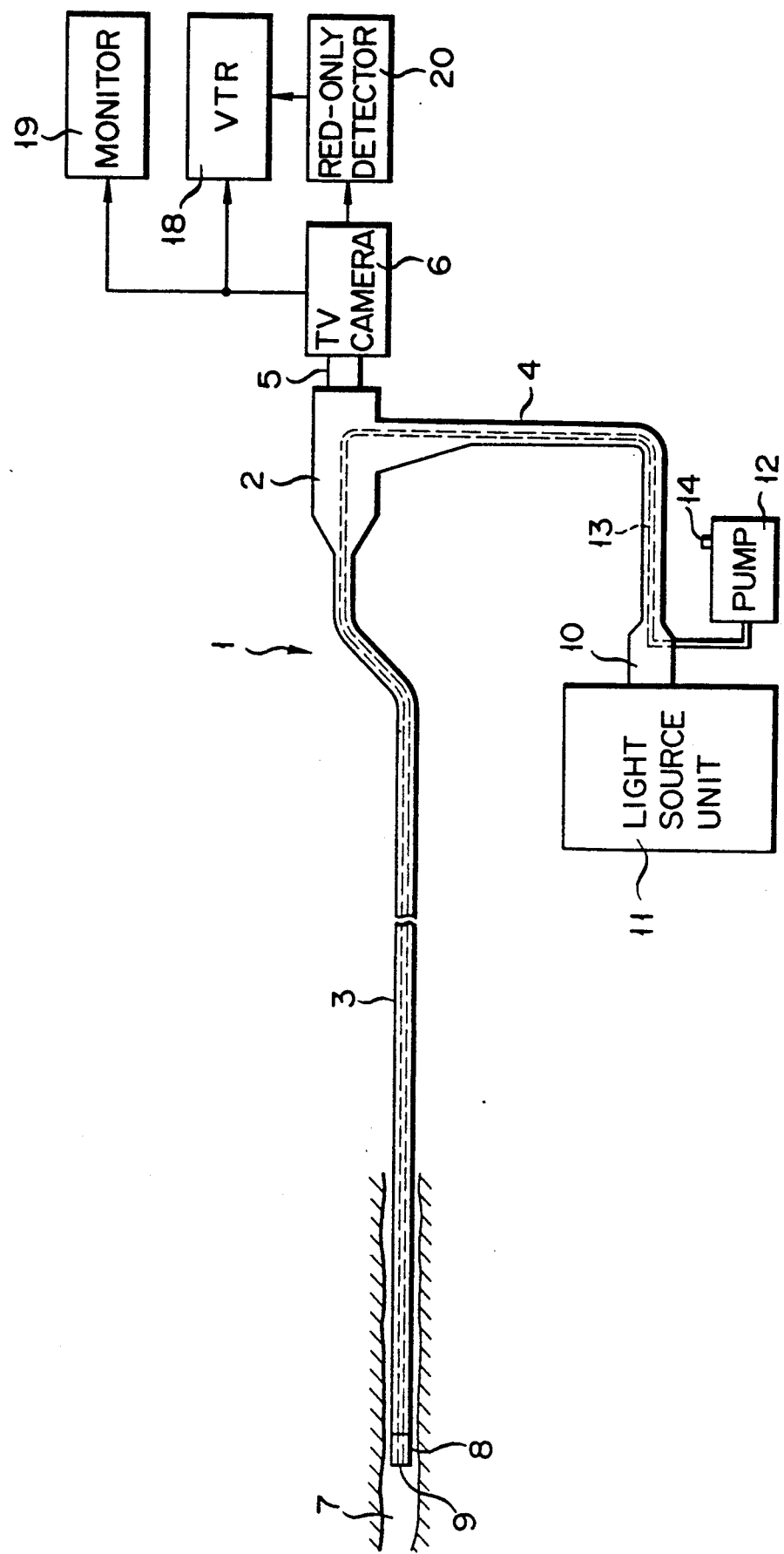
FIG. 1 is a view showing an entire structure of an intravascular endoscope apparatus according to a first embodiment of the present invention.
Figure 4:
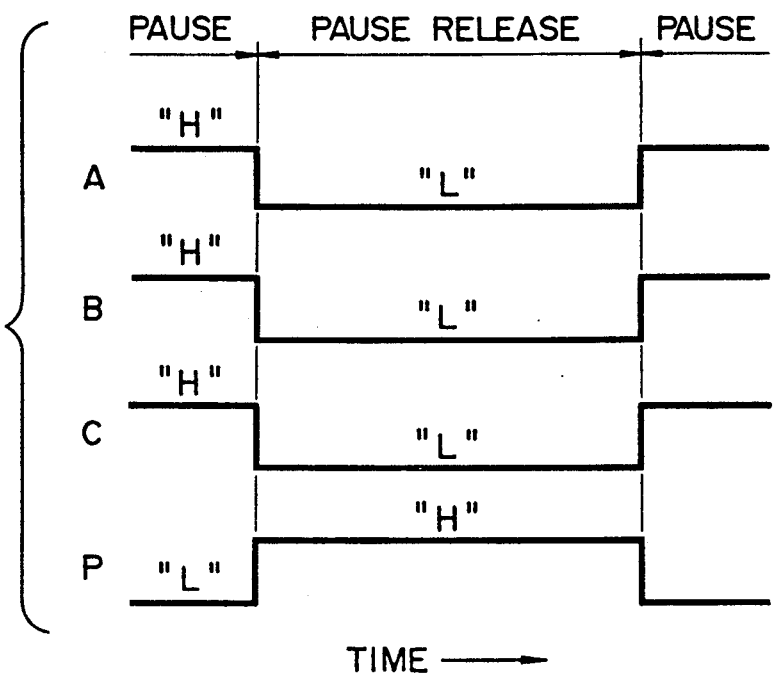
FIG. 4 is a timing chart for explaining an operation of the first embodiment.

An intravascular endoscope apparatus will be described below with reference to FIG. 1. An intravascular endoscope main body 1 includes an operation portion 2, an insert portion 3, and a light guide cable 4. An eyepiece portion 5 extends from the operation portion 2, and a color TV camera 6 is mounted to the eyepiece portion 5. The insert portion 3 has a small diameter (about 2 mm) to be inserted in a blood vessel 7 of a patient. An optical observation system and an optical illumination system (neither are shown), and a fluid spray port 9 are disposed at a distal end portion 8 of the insert portion 3. A connector 10 extends from a distal end portion of the light guide cable 4. The connector 10 is detachably connected to a light source unit 11 and a fluid supply means such as a pump 12. The light source unit 11 generates an illumination light to be guided in the optical illumination system of the endoscope main body 1. The pump 12 supplies a fluid such as a physiological saline solution to the fluid spray port 9 through a liquid supply tube 13 of the endoscope main body 1. In other words, the pump 12 and the liquid supply tube 13 constitute the fluid supply means. The pump 12 has an operation switch 14. When the operation switch 14 is turned on, the pump 12 is operated and the physiological saline solution is discharged through the fluid spray port 9.

As shown in FIG. 2, the TV camera 6 outputs a video signals V, R, G, and B corresponding to an observed image obtained by the endoscope main body 1.

The video signal V output from the TV camera 6 is input to a well-known video tape recorder (to be referred to as a VTR hereinafter) 18 which has a pause function and to a monitor 19. The VTR 18 constitutes an image recording unit together with the TV camera 6, and records the video signal V on a recording medium such as a video tape (not shown). In adition, the VTR 18 includes a means for controlling an ON/OFF operation mode of a recording operation thereof in accordance with a detection result of a color tone detecting means to be described later such as a red-only detector 20. The monitor 19 displays the video signal V as an actual image.

The TV camera 6 outputs the red video signal R corresponding to a red image, the green video signal G corresponding to a green image, and the blue video signal B corresponding to a blue image.

These video signals R, G, and B are supplied to the red-only detector 20. Note that a total voltage of these video signals R, G, and B is 0.7 V.

The red-only detector 20 detects a specific color tone image such as a red image of the image observed by the endoscope main body 1. The detailed arrangement of the red-only detector 20 is shown in FIG. 3.

More specifically, the red video signal (R) output terminal of the TV camera 6 is connected to the inverting input terminal of a first comparator 23 through an integrating circuit including a resistor 21 and a capacitor 22. A reference voltage RVref (=0.5 V) is applied to the non-inverting input terminal of the first comparator 23. The output terminal of the first comparator 23 is connected to the first input terminal of a NAND gate 25 through an inverter 24.

The green video signal (G) output terminal of the TV camera 6 is connected to the inverting input terminal of a second comparator 33 through an integrating circuit including a resistor 31 and a capacitor 32. A reference voltage GVref (=0.2 V) is applied to the non-inverting input terminal of the second comparator 33. The output terminal of the second comparator 33 is connected to the second input terminal of the NAND gate 25.

In addition, the blue video signal (B) output terminal of the TV camera 6 is connected to the inverting input terminal of a third comparator 43 through an integrating circuit including a resistor 41 and a capacitor 42. A reference voltage BVref (=0.2 V) is applied to the non-inverting input terminal of the third comparator 43. The output terminal of the third comparator 43 is connected to the third input terminal of the NAND gate 25. Note that each integrating circuit converts the video signal, the duration of which includes a blanking period, into a DC signal. An output from the NAND gate 25 serves as an output from the red-only detector 8.

The red-only detector 20 is connected to the VTR 18 to supply the output therefrom to the VTR 18 as a recording operation control signal P.

An operation of the intravascular endoscope mechanism having the above arrangement will be described hereinafter.

First, the blood vessel 7 of a patient is partially incised. The insert portion 3 of the endoscope main body 1 is inserted into the blood vessel 7 through the incised portion. The insert portion 3 is connected to the light source unit 11 through the connector 10 extending from the distal end of the light guide cable 4 of the endoscope main body 1. An illumination light beam is guided to the optical illumination system from the light source unit 11. In this state, the TV camera 6 always monitors an image in the blood vessel 7 through the optical observation system.

At this time, the blood vessel 7 is filled with blood, and hence only the red image is observed by the TV camera 6. This observed image is converted into the video signal V by the TV camera 6, and this video signal V is supplied to the VTR 18 and the monitor 19.

The TV camera 6 also outputs the video signals R, G, and B. Since the red-only image is observed, the voltage of the red video signal R is about 0.6 V, and the voltage of each of the green and blue video signals G and B is about 0.1 V.

As described above, the reference voltages RVref, GVref, and BVref are respectively set at 0.5 V, 0.2 V, and 0.2 V. Therefore, in the red-only detector 20, the output from the first comparator 23 is set at low level "L", and the outputs from the inverter 24, the second and third comparators 33 and 43 are set at high level "H". In other words, signals A, B, and C are set at high level "H".

When the signals A, B, and C are set at high level "H", an output signal from the NAND gate 25, i.e., the operation control signal P, is set at low level "L". At this time, the VTR 18 is paused, and an operation thereof is interrupted.

More specifically, when the blood vessel 7 is filled with blood and the field of view is not assured, the observed image is not recorded.

When the operation switch 14 is turned on, the pump 12 is operated and a physiological saline solution is sprayed into the blood vessel 7 from the fluid spray port 9 through the liquid supply tube 13. The blood is scattered and the field of view is assured.

At this time, the image observed by the TV camera 6 is an observed image having a whitish detail (a red color is often mixed), and at least one of the signals A, B, and C is set at low level "L" in the red-only detector 20. Then, the operation control signal P is set at high level "H".

When the operation control signal P is set at high level "H", the pause state of the VTR 18 is released, and the operation is restarted. In other words, when the field of view is assured, the image observed by the TV camera 6 is recorded by the VTR 18.

When the operation switch 14 is turned off, a spray operation of the physiological saline solution is interrupted, and the blood vessel 7 is gradually filled with blood, so that a red-only observed image is obtained. Then, as described above, the operation control signal P is set at low level "L", and the VTR 18 is paused, thus interrupting the operation thereof.

More specifically, even if a sufficient field of view cannot be assured, the observed image is recorded by the VTR 18. Only when no field of view can be assured, a recording operation of the observed image is stopped.

Thus, when the field of view in the blood vessel 7 is not assured, the observed image is not recorded on the VTR 18. Only when the field of view is assured, the observed image is recorded by the VTR 18. Therefore, a video tape can be effectively used without waste, thus achieving an economical recording operation.

In addition, after the spray operation of the physiological saline solution is stopped, only when a small field of view can be assured, the recording operation of the observed image is continued. Therefore, a necessary and effective image can be recorded without failure, and the spray operation of the physiological saline solution and the recording operation need not be repeated. Therefore, it is convenient for a busy operator that a recording time can be shortened.

Figure 5:
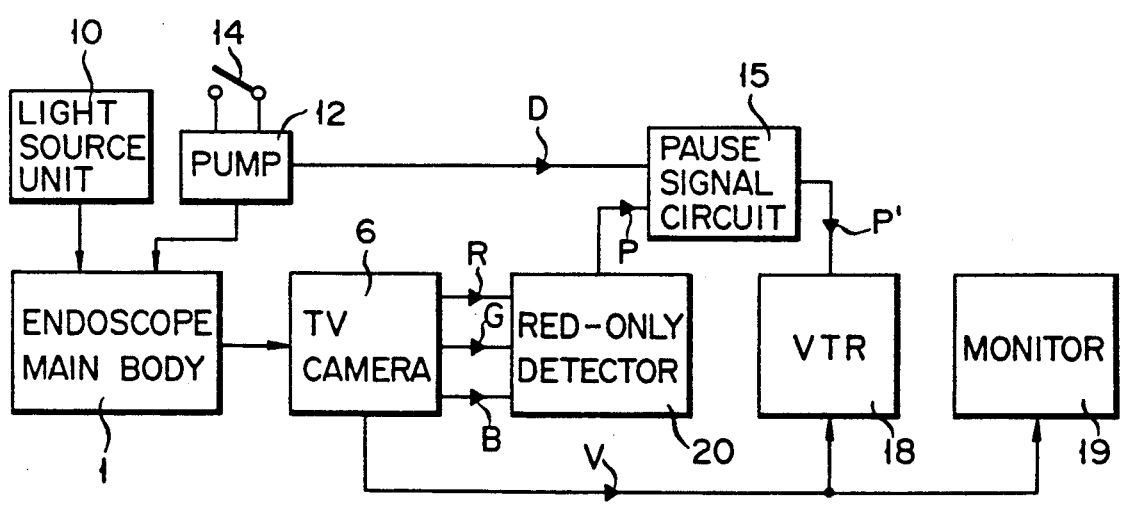
FIG. 5 is a block diagram showing an intravascular endoscope apparatus according to a second embodiment of the present invention.

A second embodiment of the present invention will be described below with reference to FIGS. 5 to 7. The same reference numerals in FIG. 5 denote the same parts as in FIG. 2, and a description thereof will be omitted.

In the second embodiment, a pause signal circuit 15 is provided. The pause signal circuit 15 receives an operation control signal P output from a red-only detector 20 and an operation state signal D output from a pump 12. An operation control signal P' can be obtained from the pause signal circuit 15, and the operation control signal P' is supplied to a VTR 18.

Figure 6:
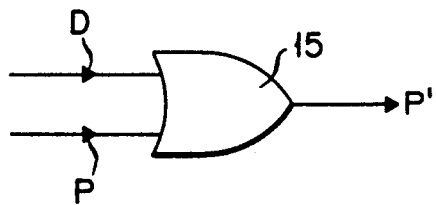
FIG. 6 is a circuit diagram of a pause signal circuit of the second embodiment.

The pause signal circuit 15 comprises, e.g., an OR gate, as shown in FIG. 6. When the operation control signal P upon detection of a red color by the red-only detector 20, or the operation state signal D during an operation of the pump 12, is input to the pause signal circuit 15, a pause state release signal P' is output.

When an operation switch 14 is turned on, the operation state signal D is set at high level "H", and when the switch 14 is turned off, the signal D is set at low level "L".

Figure 7:
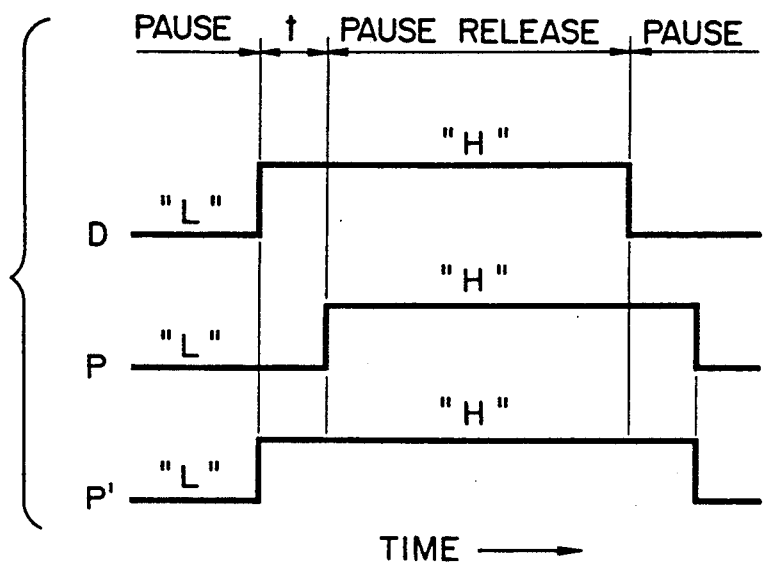
FIG. 7 is a timing chart for explaining an operation of the second embodiment.

More specifically, as shown in FIG. 7, when the operation switch 14 is turned on and a spray operation of the physiological saline solution is started, the operation state signal D is simultaneously set at high level "H". Then, the pause state release signal P' is set at high level "H", and the recording operation of the observed image is started (t before the start time of the first embodiment).

A state wherein the blood vessel 7 is filled with blood and a field of view cannot be assured and a situation wherein a physiological saline solution is mixed in the blood and assurance of the field of view is started can be confirmed.

Figure 8:
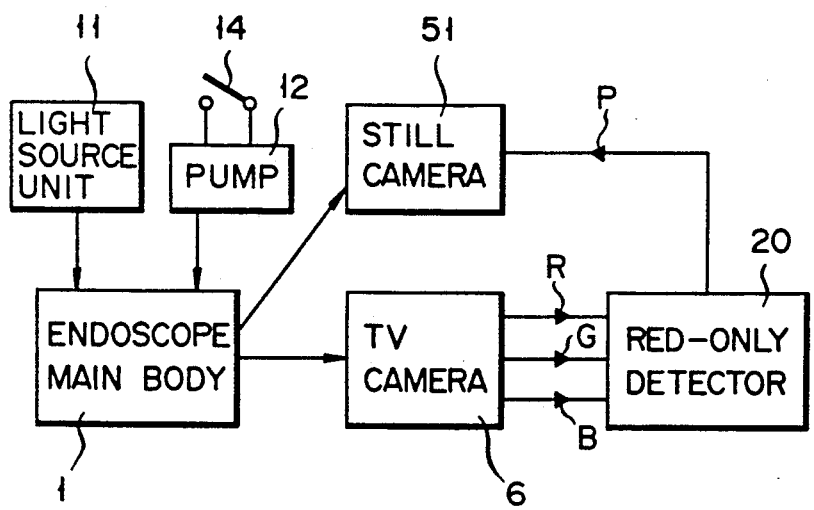
FIG. 8 is a block diagram showing an intravascular endoscope apparatus according to a third embodiment of the present invention.

A third embodiment of the present invention will be described hereinafter with reference to FIG. 8. The reference numerals in FIG. 8 denote the same parts as in FIG. 2, and a description thereof will be omitted.

In the third embodiment, a still camera 51 is employed in place of a VTR 18 as an image recording unit. An image observed by an endoscope main body 1 is supplied to a TV camera 6 and the still camera 51 by a half mirror (not shown). An operation control signal P output from a red-only detector 20 is supplied to the still camera 51.

The still camera 51 records an image (still image), observed by the endoscope main body 1, on a recording medium such as a film (not shown). Since the still camera 51 includes a motor drive or a winder, a continuous photographing operation can be performed.

The still camera 51 includes a means for controlling an ON/OFF operation state of the continuous photographing operation thereof in accordance with a detection result of the red-only detector 20 to be described later. More specifically, the operation of the endoscope in the third embodiment is the same as that in the first embodiment except that the images of the endoscope main body 1 are recorded by a continuous photographing operation using the still camera 51.

Note that although a fiberscope is used as the endoscope main body 1 in the above embodiments, an electronic endoscope can be used, as a matter of course. In this case, the TV camera 6 is not required.

Although the VTR 18 or the still camera 51 is used as an image recording unit, the present invention is not limited thereto, and a so-called image memory such as an optical or magnetic disk unit may be employed.

What is claimed is:

1. An intravascular endoscope apparatus, comprising:
    an endoscope main body, having an insert portion to be inserted into a blood vessel, for observing the interior of the blood vessel;
    fluid supplying means, coupled to said endoscope main body, for spraying a fluid through said insert portion;
    image recording means, coupled to said endoscope main body, for recording an image observed by said endoscope main body;
    color tone detecting means for detecting a color tone of the image observed by said endoscope main body; and
    control means for controlling an operation state of said image recording means in accordance with a detection result of said color tone detecting means.

2. An apparatus according to claim 1, wherein said image recording means includes a TV camera and a video tape recorder.

3. An apparatus according to claim 1, wherein:
    said image recording means comprises a still camera; and
    said color tone detecting means comprises a red-only detector.

4. An apparatus according to claim 3, wherein said still camera includes means for starting and interrupting a photographing operation in response to an output signal from said red-only detector.

5. An apparatus according to claim 1, wherein said color tone detecting means comprises a red-only detector.

6. An apparatus according to claim 5, wherein said red-only detector comprises:
   a first comparator means for comparing a voltage of a red-video signal output from said TV camera with a reference voltage of a first level;
   second comparator means for comparing a voltage of a green video signal with a reference voltage of a second level; and
   third comparator means for comparing a voltage of a blue video signal with said reference voltage of said second level;
   said first, second and third comparator means being arranged such that an output terminal of said first comparator means is connected to a first input terminal of a NAND gate through an inverter, an output terminal of said second comparator means is connected to a second input terminal of said NAND gate, an output terminal of said third comparator means is connected to a third input terminal of said NAND gate, and said NAND gate outputting an operation control signal for controlling an operation state of a video tape recorder.

7. An apparatus according to claim 1, wherein:
   said image recording means includes a video tape recorder;
   said control means is provided in said video tape recorder; and
   said color tone detecting means comprises a red-only detector for detecting a red color video signal.

8. An apparatus according to claim 7, wherein said video tape recorder has a pause function.

9. An apparatus according to claim 7, wherein:
   said fluid supplying means includes a pump;
   said control means includes a pause signal circuit; and
   said video tape recorder includes means responsive to an output from said pause signal circuit for outputting a pause state release signal when a red color is detected by said red-only detector or when said pump is operated, to thereby release said video tape recorder from a pause state and to permit recording by said video tape recorder.

10. An apparatus according to claim 9, wherein said pause signal circuit comprises an OR gate.

11. An apparatus according to claim 1, wherein said fluid supplying means includes:
    a pump; and
    a liquid supply tube for guiding a fluid discharged from said pump to said insert portion of said endoscope main body.

12. An apparatus according to claim 1, wherein said image recording means has operation states which comprise at least an image recording state and a stop state.

13. An apparatus according to claim 12, wherein said image recording means comprises a video tape recorder, and said operation states include a pause state.

* * * * *